US012589141B2

(12) United States Patent
Xi et al.

(10) Patent No.: US 12,589,141 B2
(45) Date of Patent: Mar. 31, 2026

(54) DNA VACCINE CAPABLE OF EFFECTIVELY TREATING AND/OR PREVENTING TYPE 1 DIABETES AND USE THEREOF

(71) Applicant: The Fifth Medical Center of Chinese PLA General Hospital, Beijing (CN)

(72) Inventors: Yongzhi Xi, Beijing (CN); Song Yun, Beijing (CN)

(73) Assignee: The Fifth Medical Center of Chinese PLA General Hospital, Beijing (CN)

( * ) Notice: Subject to any disclaimer, the term of this patent is extended or adjusted under 35 U.S.C. 154(b) by 944 days.

(21) Appl. No.: 17/767,291

(22) PCT Filed: Mar. 2, 2020

(86) PCT No.: PCT/CN2020/077488
§ 371 (c)(1),
(2) Date: Apr. 7, 2022

(87) PCT Pub. No.: WO2021/068452
PCT Pub. Date: Apr. 15, 2021

(65) Prior Publication Data
US 2022/0362359 A1 Nov. 17, 2022

(30) Foreign Application Priority Data
Oct. 10, 2019 (CN) .......................... 201910956530.6

(51) Int. Cl.
*A61K 39/00* (2006.01)
*A61P 3/10* (2006.01)

(52) U.S. Cl.
CPC ............ *A61K 39/0008* (2013.01); *A61P 3/10* (2018.01); *A61K 2039/53* (2013.01)

(58) Field of Classification Search
CPC ........ A61K 2039/6037; A61K 2039/53; A61K 39/0008; A61K 39/0005; A61P 3/10; C07K 14/70532; C07K 2319/00; C07K 14/195; C12N 15/86
See application file for complete search history.

(56) References Cited

U.S. PATENT DOCUMENTS 9,029,520 B2 * 5/2015 Xi ........................... A61P 37/06
435/320.1
2015/0306193 A1 * 10/2015 Czyzyk .............. C07K 14/8121
424/193.1

FOREIGN PATENT DOCUMENTS

| CN | 1498902 A | 5/2004 |
| CN | 101824424 A | 9/2010 |
| CN | 102161998 A | 8/2011 |
| CN | 110639012 A | 1/2020 |
| EP | 2 628 802 A1 | 8/2013 |

OTHER PUBLICATIONS

Lee et al. Cell Immunol. Mar. 2013;282(1):1-8.*
Dai Xin (2019). Fifth Medical Center of PLA General Hospital—New breakthrough in type 1 diabetes treatment, p. 7 (English Translation Provided).
Shao Chenglei Zhang Ling (2004). Research progress on treatment of type diabetes mellitus, Department of Medicinal Chemistry, School of Pharmacy, Shandong University, Shandong Institute of Biological Medicine, pp. 6-9 (English Translation of Abstract Provided).
Xi, Yongzhi et al. (2006). "Molecular Construction and Characterization of a Novel Exotoxin Fusion Protein that Selectively Blocks the B7:CD28 Costimulatory Signal System," J. Immunother. 29:586-595.

* cited by examiner

*Primary Examiner* — Bao Q Li
(74) *Attorney, Agent, or Firm* — Cooley LLP

(57) ABSTRACT

Provided is use of a recombinant nucleic acid construct containing a B7-2-PE40 exotoxin fusion gene in the preparation of a DNA vaccine or medicament for treatment and/or prevention of type 1 diabetes. The DNA vaccine can reduce blood glucose in patient with type 1 diabetes, restore the secretion of insulin of the patients per se, and reduce the contents of islet cell autoantibody (ICA) and glutamate decarboxylase autoantibody (GAD) in the patients.

10 Claims, 10 Drawing Sheets

Specification includes a Sequence Listing.

B7-2-pe40 sequencing and open reading framework

1 gctagcgtttaacttaagcttggtacctgtt          *Kpn*I restriction site 32 atggatggactgagtaacattctctttgtgatggccttcctgctc     Initiation codon and signal peptide M   D   G   L   S   N   I   L   F   V   M   A   F   L   L
77 tctggtgctgctcctctgaagattcaagcttatttcaatgagact
   S   G   A   A   P   L   K   I   Q   A   Y   F   N   E   T
122 gcaggcctgccgtgccaatttgcaaactctcaaaaccaaagcctg
   A   G*   L   P   C   Q   F   A   N   S   Q   N   Q   S   L
167 agtgagctagtagtatttggcaggaccaggaaaacttggttctg
   S   E   L   V   V   F   W   Q   D   Q   E   N   L   V   L
212 aatgaggtatacttaggcaaagagaaatttgacagtgttcattcc
   N   E   V   Y   L   G   K   E   K   F   D   S   V   H   S
257 aagtatatgggccgcacaagttttgattcggacagttggaccctg
   K   Y   M   G   R   T   S   F   D   S   D   S   W   T   L
302 agacttcacaatcttcagatcaaggacaagggcttgtatcaatgt
   R   L   H   N   L   Q   I   K   D   K   G   L   Y   Q   C
347 atcatccatcacaaaaagcccacaggaatgattcgcatccaccag
   I   I   H   H   K   K   P   T   G   M   I   R   I   H   Q
392 atgaattctgaactgtcagtgcttgctaacttcagtcaacctgaa
   M   N   S   E   L   S   V   L   A   N   F   S   Q   P   E
437 atagtaccaatttctaatataacagaaaatgtgtacataaatttg
   I   V   P   I   S   N   I   T   E   N   V   Y   I   N   L
482 acctgctcatctatacgcggttacccagaacctaagaagatgagt
   T   C   S   S   I   R   G   Y   P   E   P   K   K   M   S
527 gttttgctaagaaccaagaattcaactatcgagtatgatggtatt
   V   L   L   R   T   K   N   S   T   I   E   Y   D   G   I
572 atgcagaaatctcaagataatgtcacagaactgtacgacgtttcc
   M   Q   K   S   Q   D   N   V   T   E   L   Y   D   V   S
617 atcagcttgtctgtttcattccctgatgttgcgagcaatatgacc
   I   S   L   S   V   S   F   P   D   V   A   S   N   M   T
662 atcttctgtattctggaaactgacaagacgcggctttatcttca
   I   F   C   I   L   E   T   D   K   T   R   L   L   S   S
707 cctttctctatagagcttgaggaccctcagcctcccccagaccag
   P   F   S   I   E   L   E   D   P   Q   P   P   P   D   Q
752 attcctggtggcggcggatctggaggcggtggaagcggtggcggt
   I   P   G   G   G   G   S   G   G   G   G   S   G   G   G
797 ggctcgggcggtggtgggtcgggcggcagcctggccgcgctgacc
   G   S   G   G   G   G   S   G   G   S   L   A   A   L   T
842 gcgcaccaggcttgccacctgccgctggagacttccacccgtcat
   A   H   Q   A   C   H   L   P   L   E   T   S*   T   R   H
887 cgccagccgcgcggctgggaacaactggagcagtgcggctatccg
   R   Q   P   R   G   W   E   Q   L   E   Q   C   G   Y   P
932 gtgcagcggctggtcgccctctacctggcggcgcggctgtcgtgg
   V   Q   R   L   V   A   L   Y   L   A   A   R   L   S   W
977 aaccaggtcgaccaggtgatccgcaacgccctggccagccccggc
   N   Q   V   D   Q   V   I   R   N   A   L   A   S   P   G
1022 agcggcggcgacctgggccgaagcgatccgcgagcagccggagcag
   S   G   G   D   L   G   E   A   I   R   E   Q   P   E   Q
1067 gcccgtcttgccctgaccctggccgccgccgagagcgagcgcttc
   A   R   L   A   L   T   L   A   A   A   E   S   E   R   F
1112 gtccggcagggcaccggcaacgacgaggccggcgcggccaacgcc
   V   R   Q   G   T   G   N   D   E   A   G   A   A   N   A
1157 gacgtggtgagcctgacctgcccggtcgccgccggtgaatgcgcg
   D   V   V   S   L   T   C   P   V   A   A   G   E   C   A
1202 ggccccgccggacagcggctacgccctgctggagcgcaactatccc
   G   P   A   D   S   G   Y   A   L   L   E   R   N   Y   P

Fig. 5A

1247 actggcgcggagttcctcggcgacggcggcgacgtcagcttcagc
     T   G   A   E   F   L   G   D   G   G   D   V   S   F   S
1292 acccgcggcacgcagaactggacggtggagcggctgctccaggcg
     T   R   G   T   Q   N   W   T   V   E   R   L   L   Q   A
1337 caccgccaactggaggagcgcggctatgtgttcgtcggctaccac
     H   R   Q   L   E   E   R   G   Y   V   F   V   G   Y   H
1382 ggcaccttcctcgaagcggcgcaaagcatcgtcttcggcggggtg
     G   T   F   L   E   A   A   Q   S   I   V   F   G   G   V
1427 cgcgcgcgcaaccaggacctcgacgcgatctggcgcgggtttctat
     R   A   R   N   Q   D   L   D   A   I   W   R   G   F   Y
1472 atcgccggcgatccggcgctggcctacggctacgcccaggaccag
     I   A   G   D   P   A   L   A   Y   G   Y   A   Q   D   Q
1517 gaacccgacgcacgcggccggatccgcaacggtgccctgctgcgg
     E   P   D   A   R   G   R   I   R   N   G   A   L   L   R
1562 gtctatgtgccgcgctcgagcctgccgggcttctaccgcaccagc
     V   Y   V   P   R   S   S   L   P   G   F   Y   R   T   S
1607 ctgaccctggccgcgccggaggcggcgggcgaggtcgaacggctg
     L   T   L   A   A   P   E   A   A   G   E   V   E   R   L
1652 atcggccatccgctgccgctgcgcctggacgccatcaccggcccc
     I   G   H   P   L   P   L   R   L   D   A   I   T   G   P
1697 gaggaggaaggcgggcgcctggagaccattctcggctggccgctg
     E   E   E   G   G   R   L   E   T   I   L   G   W   P   L
1742 gccgagcgcaccgtggtgattccctcggcgatccccaccgacccg
     A   E   R   T   V   V   I   P   S   A   I   P   T   D   P
1787 cgcaacgtcggcggcgacctcgacccgtccagcatccccgacaag
     R   N   V   G   G   D   L   D   P   S   S   I   P   D   K
1832 gaacaggcgatcagcgccctgccggactacgccagccagcccggc
     E   Q   A   I   S   A   L   P   D   Y   A   S   Q   P   G
1877 aaaccgccgcgcgaggacctgaaginatctagaggcccgtaac
     K   P   P   R   E   D   L   K   *

Stop codon and *Xba* I restriction site

Fig. 5B

SEQUENCE LISTING

```
<160> NUMBER OF SEQ ID NOS: 5

<210> SEQ ID NO 1
<211> LENGTH: 1919
<212> TYPE: DNA
<213> ORGANISM: Artificial Sequence
<220> FEATURE:
<223> OTHER INFORMATION: B7-2-PE40 exotoxin fusion gene

<400> SEQUENCE: 1
gctagcgttt aacttaagct tggtacctgt tatggatgga ctgagtaaca ttctctttgt        60
gatggccttc ctgctctctg gtgctgctcc tctgaagatt caagcttatt tcaatgagac       120
tgcaggcctg ccgtgccaat ttgcaaactc tcaaaaccaa agcctgagtg agctagtagt       180
```

```
attttggcag gaccaggaaa acttggttct gaatgaggta tacttaggca aagagaaatt      240
tgacagtgtt cattccaagt atatgggccg cacaagtttt gattcggaca gttggaccct      300
gagacttcac aatcttcaga tcaaggacaa gggcttgtat caatgtatca tccatcacaa      360
aaagcccaca ggaatgattc gcatccacca gatgaattct gaactgtcag tgcttgctaa      420
cttcagtcaa cctgaaatag taccaatttc taatataaca gaaaatgtgt acataaattt      480
gacctgctca tctatacgcg gttacccaga acctaagaag atgagtgttt tgctaagaac      540
caagaattca actatcgagt atgatggtat tatgcagaaa tctcaagata atgtcacaga      600
actgtacgac gtttccatca gcttgtctgt ttcattccct gatgttgcga gcaatatgac      660
catcttctgt attctggaaa ctgacaagac gcggctttta tcttcacctt tctctataga      720
gcttgaggac cctcagcctc ccccagacca gattcctggt ggcggcggat ctggaggcgg      780
tggaagcggt ggcggtggct cgggcggtgg tgggtcgggc ggcagcctgg ccgcgctgac      840
cgcgcaccag gcttgccacc tgccgctgga gacttccacc cgtcatcgcc agccgcgcgg      900
ctgggaacaa ctggagcagt gcggctatcc ggtgcagcgg ctggtcgccc tctacctggc      960
ggcgcggctg tcgtggaacc aggtcgacca ggtgatccgc aacgccctgg ccagccccgg     1020
cagcggcggc gacctgggcg aagcgatccg cgagcagccg gagcaggccc gtcttgccct     1080
gaccctggcc gccgccgaga gcgagcgctt cgtccggcag ggcaccggca acgacgaggc     1140
cggcgcggcc aacgccgacg tggtgagcct gacctgcccg gtcgccgccg gtgaatgcgc     1200
gggcccggcg gacagcggct acgccctgct ggagcgcaac tatcccactg gcgcggagtt     1260
cctcggcgac ggcggcgacg tcagcttcag cacccgcggc acgcagaact ggacggtgga     1320
gcggctgctc caggcgcacc gccaactgga ggagcgcggc tatgtgttcg tcggctacca     1380
cggcaccttc ctcgaagcgg cgcaaagcat cgtcttcggc ggggtgcgcg cgcgcaacca     1440
ggacctcgac gcgatctggc gcggtttcta tatcgccggc gatccggcgc tggcctacgg     1500
ctacgcccag gaccaggaac ccgacgcacg cggccggatc cgcaacggtg ccctgctgcg     1560
ggtctatgtg ccgcgctcga gcctgccggg cttctaccgc accagcctga ccctggccgc     1620
gccggaggcg gcgggcgagg tcgaacggct gatcggccat ccgctgccgc tgcgcctgga     1680
cgccatcacc ggccccgagg aggaaggcgg gcgcctggag accattctcg gctggccgct     1740
ggccgagcgc accgtggtga ttccctcggc gatccccacc gacccgcgca cgtcggcggg     1800
cgacctcgac ccgtccagca tccccgacaa ggaacaggcg atcagcgccc tgccggacta     1860
cgccagccag cccggcaaac gccgcgcgcga ggacctgaag taatctagag gcccgtaac     1919
```

```
<210> SEQ ID NO 2
<211> LENGTH: 86
<212> TYPE: DNA
<213> ORGANISM: Artificial Sequence
<220> FEATURE:
<223> OTHER INFORMATION: upstream primer P1

<400> SEQUENCE: 2
cggggtacct gttatggatg gactgagtaa cattctcttt gtgatggcct tcctgctctc       60
tggtgctgct cctctgaaga ttcaag                                            86

<210> SEQ ID NO 3
<211> LENGTH: 36
<212> TYPE: DNA
<213> ORGANISM: Artificial Sequence
<220> FEATURE:
```

-continued

```
<223> OTHER INFORMATION: downstream primer P2

<400> SEQUENCE: 3
gctctagatt acttcaggtc ctcgcgcggc ggtttg                              36

<210> SEQ ID NO 4
<211> LENGTH: 20
<212> TYPE: DNA
<213> ORGANISM: Artificial Sequence
<220> FEATURE:
<223> OTHER INFORMATION: upstream primer P5

<400> SEQUENCE: 4
agaaaatctg gcaccacacc                                                20

<210> SEQ ID NO 5
<211> LENGTH: 20
<212> TYPE: DNA
<213> ORGANISM: Artificial Sequence
<220> FEATURE:
<223> OTHER INFORMATION: downstream primer P6

<400> SEQUENCE: 5
agcactgtgt tggcgtacag                                                20
```

DNA VACCINE CAPABLE OF EFFECTIVELY TREATING AND/OR PREVENTING TYPE 1 DIABETES AND USE THEREOF

RELATED APPLICATIONS

The present application is a U.S. National Phase Application, filed under 35 U.S.C. § 371, of International Application No. PCT/CN2020/077488, filed Mar. 2, 2020, which claims priority to, and the benefit of, Chinese Patent Application No. 201910956530.6, filed Oct. 10, 2019, the entirety of the disclosure of each of which is incorporated herein by reference.

INCORPORATION OF THE SEQUENCE LISTING

The instant application contains a sequence listing of the text file submitted electronically herewith and is hereby incorporated by reference in its entirety: a computer readable format copy of the Sequence Listing (filename: CCPI_024_00US_SeqList_ST25.txt, date recorded Apr. 6, 2022, file size 4 kb).

TECHNICAL FIELD

The present invention relates to a DNA vaccine for the treatment of type 1 diabetes and its use, in particular to a use of a recombinant nucleic acid construct containing a B7-PE40 fusion gene for preparing a DNA vaccine for the treatment and/or prevention of type 1 diabetes.

BACKGROUND

Type 1 diabetes is a refractory and heterogeneous metabolic and autoimmune disease that seriously endangers human health and life safety. The latest international big-data research shows that since the beginning of the 21$^{st}$ century, the incidence of type 1 diabetes in the world has continued to increase. Since 2010, in Asia, Europe and North America, it increased by a rate of 4.0%, 3.2% and 5.3%, respectively. Comparatively speaking, the research on the epidemiology of type 1 diabetes in China is not very late in nature. As early as more than 20 years ago, at the end of the last century, scientific research institutes also conducted extensive research and investigation on the epidemiology of type 1 diabetes in China, but due to the incompleteness and imperfection of the research data at that time, the final statistical results and conclusions were only based on the data voluntarily reported by some hospitals in 22 cities. In order to ensure the accuracy of the survey results of the overall incidence of type 1 diabetes in China, a team led by Professor Weng Jianping, former chairman of the Diabetes Branch of the Chinese Medical Association, joined 505 hospitals in 13 regions in China to participate in the "Type 1 diabetes study covering all ages from 2010 to 2013 in China"; after unremitting efforts for about 3 years, the data of 133 million people were collected, which covered about 10% of the total population of China, including 6% of children and adolescents under the age of 15. In the study, a total of 5018 new cases of type 1 diabetes was collected, of which 65.3% of the patients were over the age of 20. The final research results show that there are at least 10 million patients with type 1 diabetes in China. The incidence rate is 0.69/100,000. That is, there are about 13,000 new cases of type 1 diabetes in China each year, of which more than 9,000 are in people over the age of 15. Most cases of new-onset type 1 diabetes are diagnosed in adulthood. The incidence of type 1 diabetes in children and adolescents aged 0-14 years is significantly related to latitude, and the incidence is higher in the north than in the south, but the incidence in people over 15 years old is not related to the change in latitude. This may be related to genetic and environmental factors. It can be seen that the incidence of type 1 diabetes in China and the total number of patients are much higher than previous conclusions. The research results were published online on Jan. 4, 2018 in the internationally renowned authoritative medical journal "British Medical Journal" and the website of the American Association for the Advancement of Science.

With the continuous research and in-depth understanding of the etiology and pathogenesis of diabetes, the classification of diabetes has become more scientific and accurate. After continuous revision and improvement by the National Diabetes Data Group (NDDG), the American Diabetes Association (ADA), the International Diabetes Federation-West Pacific Region (IDF-WPR) Committee and the World Health Organization (WHO), the classification of diabetes has evolved from the simple and extensive classification method of type 1 and type 2 in 1936 to the WHO diabetes etiology classification method recognized and officially adopted by all countries in the world, that is, diabetes can be divided into 4 types: type 1 diabetes (insulin-dependent diabetes), type 2 diabetes (non-insulin dependent diabetes), gestational diabetes and other special types of diabetes. According to the latest international classification principles of etiology of diabetes, the original classification terms of "insulin-dependent diabetes mellitus" and "non-insulin-dependent diabetes mellitus" have been cancelled to avoid confusing the concept of classification by treatment. Type 1 and Type 2 as typing nouns are retained, and the Roman numerals I and II are no longer used. With the rapid development of human genomics, molecular biology, human genetics, immunopathology and other disciplines, special types of diabetes can be divided into 8 subcategories, and there are more detailed branches in the subcategories. At least 27 types of monogenic diabetes alone have been identified so far, and these types of diabetes have previously been mistaken for either type 2 or type 1. Type 1 diabetes, also known as insulin-dependent diabetes, is not only a refractory metabolic disease. From the perspective of its pathogenesis, it also belongs to the category of autoimmune diseases. Recently, the international academic community also defined it as a class of important autoimmune diseases (IAIDs).

Up to now, the traditional mainstream treatment strategy for type 1 diabetes in the world has always been long-term supplementary therapy with insulin or insulin analogs, which is the basis for ensuring that patients with type 1 diabetes can have a good quality of life and satisfactory control of metabolic level. However, long-term use of insulin often brings many serious side effects, especially hypoglycemia reaction or hypoglycemia coma and insulin resistance. In recent years, there has been considerable progress in the research and application of new strategies for the treatment of type 1 diabetes in the world, such as the exploration of whole pancreas transplantation, islet cell transplantation, transplantation of islet 13 cells derived from adult stem cells or embryonic stem cells by in vitro induction and differentiation, gene therapy, and the application of immunosuppressants or immunomodulators, etc., but due to the limitations of various conditions or technical imperfections and immaturity, these new therapies have not been able to form a dominant clinical treatment plan or strategy, and thus are not widely used. Therefore, how to improve or overcome the drawbacks of the above-mentioned drugs or therapies, or create a new generation of drugs or therapies that can specifically treat type 1 diabetes has become the primary problem that urgently needs to be solved! In recent years, international research on the treatment of type 1 diabetes tends to focus on the pathogenesis of type 1 diabetes, and exploring new strategies for developing therapeutic DNA vaccines has become the focus and hotspot in this field. In 2000, 2008 and 2012, the NIH in the United States listed for three times the development of new targeted immune suppressive/modulatory agents, especially therapeutic DNA vaccines, for important autoimmune diseases (including type 1 diabetes) as the top priority of major issues, and gave priority to funding and open tenders to the United States and European Union countries.

CONTENTS OF THE INVENTION

The inventors found in research that after the recombinant nucleic acid construct pcDNA3.1/Zeo(+)-B7-2-PE40 was transfected into a eukaryotic cell and was subjected to transcription, translation and post-translational modification, B7-2-PE40 was secreted extracellularly; and that the pcDNA3.1/Zeo(+)-B7-2-PE40 could highly express B7-2-PE40 in the eukaryotic cell and the expression product had good targeted immunosuppressive activity; and the inventors also found that a DNA vaccine comprising pcDNA3.1/Zeo(+)-B7-2-PE40 comprising an exotoxin fusion gene could effectively treat and/or prevent type 1 diabetes in rats. The present invention has been completed based on these findings.

Accordingly, the various aspects and features provided by the present invention are summarized as follows:

One aspect of the present invention relates to a use of a recombinant nucleic acid construct containing a B7-2-PE40 exotoxin fusion gene in the manufacture of a DNA vaccine for the treatment and/or prevention of type 1 diabetes. Such a DNA vaccine can be used for the treatment and/or prevention of a mammalian subject suffering from or at risk of developing type 1 diabetes. Preferably, the fusion gene has a sequence as shown in SEQ ID NO:1.

In a specific embodiment of the present invention, the recombinant nucleic acid construct contained in the DNA vaccine contains a B7-2-PE40 exotoxin fusion gene operably linked to a recombinant expression vector selected from the group consisting of pcDNA3.1/Zeo(+), pVAX1, pWL-NEO, pSV2CAT, pOG44, pXT1, pSG, pSVK3, pBPV, pMSG, pSVL and adenovirus vector, preferably; the recombinant expression vector is pcDNA3.1/Zeo(+). Preferably, the fusion gene has a sequence as shown in SEQ ID NO:1.

In the present invention, the DNA vaccine may also comprise a pharmaceutically acceptable immune adjuvant.

In one embodiment of the present invention, the DNA vaccine is used to perform immunization by injection, mucosal, gene gun introduction and other manner; preferably, it is used to perform immunization by at least one manner selected from the group consisting of intravenous injection, arterial injection, intramuscular injection, subcutaneous injection, organ injection, intrapleural injection and intraperitoneal injection.

In yet another embodiment of the present invention, the DNA vaccine is an aqueous solution or a lyophilized powder for reconstitution that can be administered via injection or mucosa route.

In another aspect, the present invention relates to a use of a recombinant nucleic acid construct containing a B7-2-PE40 exotoxin fusion gene in the manufacture of a medicament for the treatment and/or prevention of type 1 diabetes. Preferably, the fusion gene has a sequence as shown in SEQ ID NO:1.

In another aspect, the present invention also relates to a use of a recombinant nucleic acid construct containing a B7-2-PE40 exotoxin fusion gene in the manufacture of a kit or pharmaceutical composition that can be used for the treatment and/or prevention of type 1 diabetes. Preferably, the fusion gene has a sequence as shown in SEQ ID NO:1.

In yet another aspect, the present invention relates to a method for treating and/or preventing type 1 diabetes, comprising administering to a subject a therapeutically and/or prophylactically effective amount of a DNA vaccine, in which the DNA vaccine comprises a B7-2-PE40 exotoxin fusion gene that is operably linked to a vector pcDNA3.1/Zeo(+); preferably, the B7-2-PE40 exotoxin fusion gene has a sequence as shown in SEQ ID NO:1.

In yet another aspect, the present invention provides a DNA vaccine, which is used for the treatment and/or prevention of type 1 diabetes, wherein the DNA vaccine comprises a B7-2-PE40 exotoxin fusion gene that is operably linked to a vector pcDNA3.1/Zeo(+); preferably, the B7-2-PE40 exotoxin fusion gene has a sequence as shown in SEQ ID NO:1.

Definitions and Explanations of Relevant Terms in the Present Invention

In the present invention, unless otherwise specified, scientific and technical terms used herein have the meanings commonly understood by those skilled in the art. For a better understanding of the present invention, definitions and explanations of related terms are provided below.

The term "mammal" as used herein refers to a subject who may suffer from, will suffer from, or have suffered from the autoimmune disease of the present invention, including but not limited to pig, dog, cat, cattle, sheep and other livestock, and human. Preferably, the mammal is a human.

The term "prevention" as used herein refers to that the DNA vaccine of the present invention is used to prevent the occurrence of the autoimmune disease in the mammal under conditions where the autoimmune disease is likely to occur, or is imminent.

The term "treatment" as used herein refers to that the DNA vaccine of the present invention is used in the mammal to alleviate, remit, delay, prevent, eliminate or cure the autoimmune disease under the condition where the mammal has suffered from or has developed the autoimmune disease.

The term "PE40 exotoxin" used herein refers to an exotoxin commonly used in the art, which is a protein with a molecular weight of 40 kD produced by deleting the cell-binding functional domain Ia of *Pseudomonas aeruginosa* exotoxin A (PEA) with a molecular weight of 66 kD and consisting of 613 amino acids.

The term "B7-2" used herein, also known as CD86, is a member of the immunoglobulin superfamily, and is a natural ligand expressing two receptor molecules CD28/CTLA4 of the T cell surface costimulatory signaling system. B7-2 is constitutively expressed on quiescent antigen-presenting cells (APCs) and rapidly expressed on B, T, monocyte-macrophages and dendritic cells upon activation. B7-2 plays a major role in the initial phase of the immune response, in which not only the costimulatory signal produced by B7-2 binding with its corresponding receptor plays an important role in regulating T cell activation and effector cytokine secretion, but also the B7-2/CD28 axis plays a key role in the occurrence and development of autoimmune diseases such as type I diabetes mellitus and rheumatoid arthritis.

The term "B7-2-PE40 exotoxin fusion gene" as used herein refers to a fusion gene of B7-2 and PE40 exotoxin. Preferably, the fusion gene has a sequence as shown in SEQ ID NO:1.

The term "recombinant nucleic acid construct" as used herein contains a B7-2-PE40 exotoxin fusion gene and a recombinant expression vector operably linked thereto, in which the recombinant expression vector may be an eukaryotic expression vector selected from the group consisting of pcDNA3.1/Zeo(+), pVAX1, pWLNEO, pSV2CAT, pOG44, pXT1, pSG, pSVK3, pBPV, pMSG, pSVL and adenoviral vector. Preferably, the recombinant expression vector is pcDNA3.1/Zeo(+).

The term "GAD" as used herein refers to glutamate decarboxylase autoantibody, which is a synthase of inhibitory neurotransmitter γ-aminobutyric acid in the human body, and mainly present in pancreatic β-cells, GAD autoantibody is an autoantibody produced by GAD-induced immune response and is an immune indicator for the diagnosis of type 1 diabetes. The presence of GAD autoantibody indicates a lack of endogenous insulin secretion.

The term "ICA" used herein refers to islet cell autoantibody, which is an important autoantibody closely related to the occurrence, development and transition of type 1 diabetes. The autoantibody is an organ-specific antibody, and its antigen is an islet cytoplasm component or microsomal component, mainly of the IgG class, and is a marker of pancreatic β-cell damage.

The DNA vaccine of the present invention may be an aqueous solution or a lyophilized powder for reconstitution that can be administered via injection or via mucosa. Preferably, the aqueous solution or lyophilized powder for reconstitution is prepared by aseptic technique known in the art; and also preferably, they are in a sterile state during storage, transportation and use.

According to the present invention, the pharmaceutical composition can be in any pharmaceutical form known in the art that can be used for administration, including pharmaceutical composition, pharmaceutical preparation, kit and the like. Although the DNA vaccine involved in the uses described in the present invention may be administered by injection, mucosal route, etc., and these modes of administration are also part of the present invention; it will be clear to those skilled in the art that the most preferred route of administration suitable for the uses described herein is parenteral route or by injection. For the implementation of the present invention, the pharmaceutical composition is preferably a preparation for parenteral administration, including but not limited to local injection preparation and systemic injection preparation, and specific dosage forms include but are not limited to injection solution and powder for injection. More preferably, the medicament is a sterile aqueous solution for injection, or a sterile powder for reconstitution with water for injection before clinical use, especially a freeze-dried powder for injection. When preparing the freeze-dried powder for injection, it can also contain a pharmaceutically acceptable excipient, such as mannitol.

The DNA vaccine of the present invention can be introduced into an organism by a method known in the art. The introduction method includes, but is not limited to, intramuscular injection, gene gun introduction method, mucosal immunity, intravenous injection method, intraperitoneal injection method, etc. For more details, please refer to the disclosure of Alpar H O, et al. Expert Opin Drug Deliv, 2005, 2: 829-842, which is hereby incorporated by reference in its entirety.

In addition, those skilled in the art can easily determine effective doses for use in other mammals, particularly in human, based on the results of studies provided hereinafter. The one-day dose may be administered to the subject all at once throughout the day, or the desired dose may be divided into two, three, four or more sub-doses administered at appropriate intervals throughout the day. The sub-doses can be formulated in unit dosage form, for example, each unit dosage form contains an amount corresponding to appropriate subdivisions of the total daily dose. Of course, it can also be administered in a certain period of time, such as once a day, once every two days, once a week, once a month, once every two months, once every three months, once every six months, once a year, once every two years, etc.

When the DNA vaccine or pharmaceutical composition of the present invention is used in a specific clinical case, their specific dosage may be changed according to various factors, including but not limited to: severity of the disease of a subject, age, gender, body weight of a subject, route of administration, dosage form, etc.

Beneficial Effects of the Present Invention

The present invention provides a new generation of vaccine or therapy that can specifically treat and/or prevent type 1 diabetes. The DNA vaccine can significantly reduce blood sugar in a patient with type 1 diabetes, effectively restore the secretion of the patient's own insulin, and significantly reduce the contents of islet cell autoantibody (ICA) and glutamate decarboxylase autoantibody (GAD) in the patient's body, thereby achieving the effective treatment and/or prevention of type 1 diabetes. The DNA vaccine can be highly expressed in the body of patient, and the treatment efficacy can be maintained for one month by subcutaneous or intramuscular injection, thereby greatly improving the compliance of the DNA vaccine medication, and effectively avoiding the drawbacks of daily medication in type 1 diabetes patients.

BRIEF DESCRIPTION OF THE DRAWINGS

FIGS. 5A-5B show the sequence and open reading frame of B7-2-PE40.

SPECIFIC MODELS FOR CARRYING OUT THE INVENTION

Figure 1:
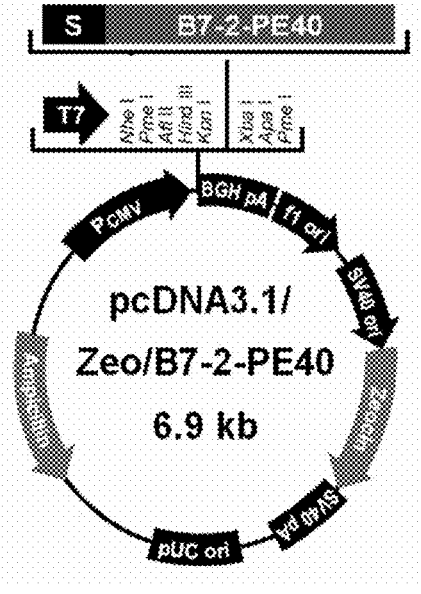
FIG. 1 shows a schematic diagram of construction the of therapeutic DNA vaccine pcDNA3.1/Zeo(+)-B7-2-PE40 eukaryotic expression vector.

The embodiments of the present invention are described in detail below with reference to the examples, but those skilled in the art will understand that the following examples are only used to illustrate the present invention and should not be regarded as limiting the scope of the present invention. If the specific conditions are not indicated in the examples, they are carried out according to the conventional conditions or the conditions suggested by the manufacturers. The reagents or instruments used without the manufacturer's indication are conventional products that can be obtained from the market.

In the examples, the expression vectors pcDNA3.1/Zeo (+), Zeocin™, Trizol and Lipofectamine™2000 were purchased from Invitrogen Company. Jurkat and Raji cell lines were purchased from ATCC (American Type Culture Collection). CHO-K1-RPE.40 cell line (Chinese hamster ovary cell anti-*Pseudomonas aeruginosa* exotoxin cell line) was also purchased from ATCC of the United States; PEA polyclonal antibody, CD86 monoclonal antibody and TMB substrate chromogenic solution were purchased from Sigma Company. PVDF membrane and Amicon Ultra-4 were purchased from Millipore Company. ECL was purchased from Pierce Corporation. MTS (CellTiter 96AQueous One Solution Cell Proliferation Assay) and PureYieild™ plasmid midiprep system were purchased from Promega. KpnI enzyme, XbaI enzyme and T4 ligase were purchased from TaKaRa Company. 2×Pfu PCR MasterMix was purchased from TIANGEN Company. QIAquick Gel Extraction Kit was purchased from QIAGEN Company.

The main instruments used in the examples were: 9700 PCR instrument (PerkinElmer), Du®640 UV detector (Beckman), Mini II protein electrophoresis instrument and protein semi-dry electrophoresis instrument (Bio-Rad), Gel-Pro3.1 Gel-Imaging System (Media Cybermetic).

Example 1. Establishment of NOD/LTJ Mouse Model of Type 1 Diabetes

Experimental group: The internationally recognized spontaneous type 1 diabetes mouse model NOD/LTJ (purchased from the Institute of Laboratory Animals, Chinese Academy of Medical Sciences) was selected and prepared according to conventional methods. Female NOD/LTJ mice, aged 7-8 week, were selected. From the $8^{th}$ week of age, trace blood in the tail tip of the mice was measured every week, and the appearance of diabetes symptoms was observed. Generally, the disease occurred within 10-12 weeks of age, and those without the disease occurred within 12 weeks of age were excluded from the experimental group. In order to accelerate the early onset of the disease in the mouse model, all female NOD/LTJ mice without disease within 8 weeks of age were injected intraperitoneally with 150 mg/kg cyclophosphamide solution for injection (Jiangsu Hengrui Medicine Co., Ltd.), and injected again with the same dose of cyclophosphamide at the week 10 to accelerate the continuous and constant onset of diabetes mellitus, and the cyclophosphamide was prepared extemporaneously with normal saline (1 mg/ml normal saline) before the injection. After such treatment with cyclophosphamide, >70% of female NOD/LTJ mice typically developed overt diabetes within 11-12 weeks of age. Thus, the experimental needs of the DNA vaccine prevention and treatment were met. Abbott micro whole blood glucose tester was used to perform weekly micro whole blood glucose measurement on the NOD/LTJ mouse model of type 1 diabetes, type 1 diabetes was diagnosed if the blood glucose measurement is greater than or equal to 11.3-13.9 for twice.

Control group: 8-week-old female BALB/c normal mice (purchased from the Animal Center of the Military Medical Research Institute) were selected.

Example 2. Construction of Therapeutic DNA Vaccine pcDNA3.1/Zeo(+)-B7-2-PE40 Eukaryotic Expression Vector The upstream primer P1 containing a signal peptide and KpnI restriction site and the downstream primer P2 containing a XbaI restriction site were designed respectively. The primer sequences were as follows:

```
Upstream primer P1:
                              (SEQ ID NO: 2)
5'-CGGGGTACCTGTTATGGATGGACTGAGTAACATTCTCTTTGTGATGGC

CTTCCTGCTCTCTGGTGCTGCTCCTCTGAAGATTCAAG-3'
```

[wherein, the single-underlined part was the KpnI restriction site; the double-underlined part was the coding sequence of initiation codon and signal peptide]

```
Downstream primer P2:
                                     (SEQ ID NO: 3)
   5'-GCTCTAGATTACTTCAGGTCCTCGCGCGGCGGTTTG-3'
```

[wherein, the single-underlined part was the XbaI restriction site]

Using the prokaryotic expression vector pRSETA-B7-2-PE40KDEL plasmid (constructed and preserved by our laboratory, see Chinese patent application 201010144610.0) as the template, high-fidelity Pfu DNA polymerase was used for PCR amplification. The amplification system was as follows:

| | |
|---|---|
| 2 × Pfu PCR Master Mix | 10 μl |
| P1 | 1 μl |
| P2 | 1 μl |
| pRSETA-B7-2-PE40KDEL(1:100) | 2 μl |
| ddH$_2$O | 6 μl |
| Total volume | 20 μl |

The PCR reaction conditions were as follows: pre-denaturation at 96° C. for 5 min, denaturation at 96° C. for 1 min, annealing at 55° C. for 1 min, extension at 72° C. for 3 min, 30 cycles, and extension at 72° C. for 10 min. 1% agarose gel electrophoresis was used for identification.

The PCR amplification product was recovered, and the recovered product and the pcDNA3.1/Zeo(+) vector were double digested with KpnI+XbaI, and the digested products were recovered after electrophoresis. The enzyme digestion system was as follows:

| | |
|---|---|
| 10 × M buffer | 2 μl |
| Xba I | 1 μl |
| Kpn I | 1 μl |
| 0.1% BSA | 2 μl |
| Recovered PCR product or pcDNA3.1/Zeo(+) vector | 10 μl |
| ddH$_2$O | 4 μl |
| Total volume | 20 μl |

After mixing, water bath at 37° C. for 3 h.

The digestion product was recovered by the steps as follows:

1) The desired band was cut from the agarose gel with a clean blade and put into a 1.5 ml Ep tube.
2) The gel was weighed, and a corresponding volume of sol solution was added in accordance with that for per 100 mg of gel, 300 μl of buffer QG was added.
3) Incubation was carried out in a 50° C. water bath for 10 minutes until the gel was completely dissolved, during which turning upside down was carried out every 2-3 minutes to mix thoroughly. After the gel was completely dissolved, the color should change to yellow.
4) 1 volume of isopropanol was added and mixed well.
5) The sample was loaded to QIAquick column and centrifuged for 1 min. The waste solution was discarded, 0.5 ml of buffer QG was added, and centrifuged for 1 min.
6) The waste solution was discarded, 0.75 ml of buffer PE was added, allowed to stand for 2 min to 5 min, and centrifuged for 1 min.
7) The waste solution was discarded, and centrifugation was carried out for 1 min. The column was then placed in a clean 1.5 ml Ep tube.

8) 30 μl of water for injection was added to the center of the column membrane, allowed to stand for 1 min, and then centrifuged for 1 min to collect the eluate.

The PCR product after double digestion was ligated to the pcDNA3.1/Zeo(+) vector, and the system was as follows:

| | |
|---|---|
| 10 × T4 Ligase buffer | 2 μl |
| T4 Ligase | 2 μl |
| Double digestion PCR product | 10 μl |
| Double digestion pcDNA3.1/Zeo(+) | 3 μl |
| ddH$_2$O | 3 μl |
| Total volume | 20 μl |

The ligation tube was placed in an ice-water mixture to perform ligation at 4° C. overnight.

The ligation product was transformed into TOP10 competent bacteria according to the following method. The specific operations were as follows:

1) 10 μl of ligation product and 20 μl of reagent A were diluted with sterile water to 100 μl, and kept on ice for later use.
2) Transformation into TOP10 competent bacteria were performed on ice (5 min), and the above-mentioned diluted plasmid for later use was added.
3) After staying on ice for 15 min, the TOP10 competent bacteria were allowed to stand at 37° C. for 1 min, coated on plate and incubated overnight at 37° C.

The positive colonies with Amp resistance were picked to extract plasmid, which was identified by double enzyme digestion (the conditions were the same as before), and the positive ones were sent to TaKaRa Company for sequencing confirmation.

The strains with the correct sequence identified were frozen and cultured in large quantities, and the PureYieild™ plasmid midi preparation kit was used to extract and purify the plasmid for DNA vaccine therapy on a large scale. The purified plasmid was dissolved in normal saline, 260/280>1.80, concentration>1.0 μg/μl.

Figure 2:
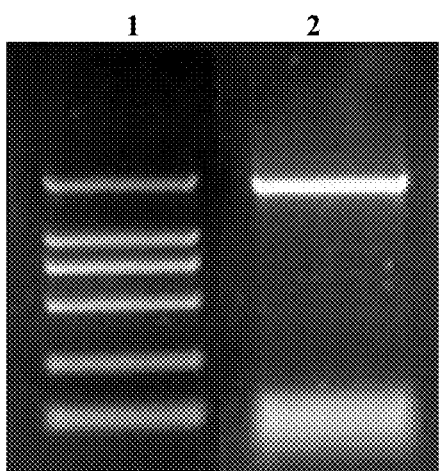
FIG. 2 shows the results of agarose electrophoresis analysis of the therapeutic DNA vaccine pcDNA3.1/Zeo(+)-B7-2-PE40 amplified by PCR. Among them, lane 1 is the DNA marker; lane 2 is the PCR amplification product of B7-2-PE40.
Figure 3:
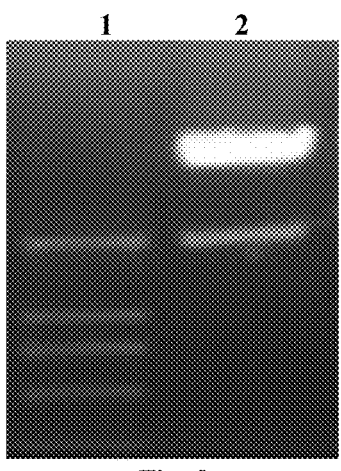
FIG. 3 shows the results of agarose electrophoresis analysis of the recombinant plasmid pcDNA3.1/Zeo(+)-B7-2-PE40 digested by KpnI and XbaI. Among them, lane 1 is the DNA marker; lane 2 is the recombinant plasmid digested by KpnI and XbaI.
Figure 4:
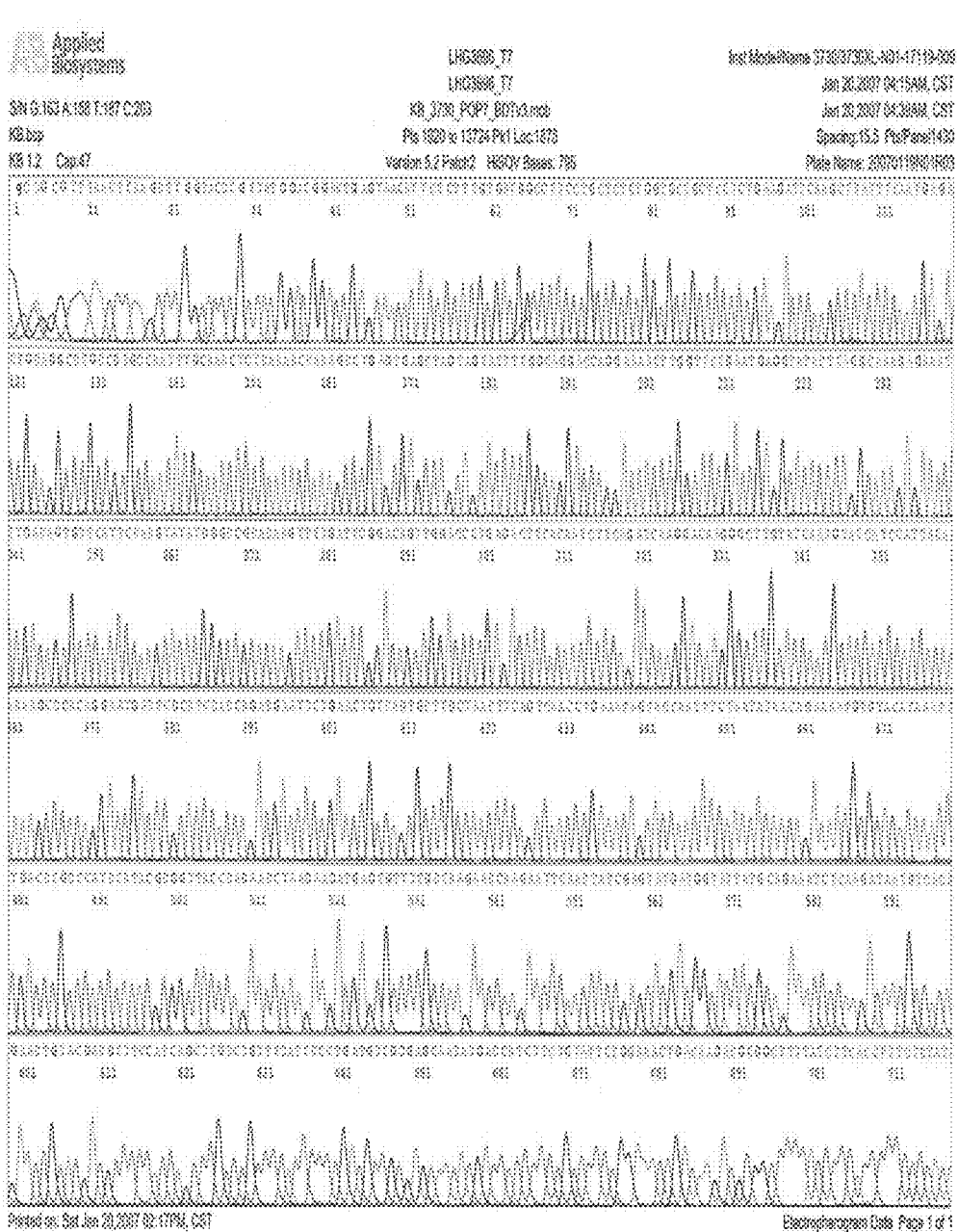
FIG. 4 shows the gene sequencing map of the therapeutic DNA vaccine pcDNA3.1/Zeo(+)-B7-2-PE40 eukaryotic expression vector.

In order to ensure the expression of B7-2-PE40 exotoxin fusion gene in eukaryotic cells, an eukaryotic expression vector pcDNA3.1/Zeo(+)-B7-2-PE40 containing B7-2-PE40 and Zeo resistance gene was constructed as shown in FIG. 1. Human B7-2-PE40 was amplified with the designed PCR primers, and the amplified product was analyzed by agarose gel electrophoresis, and a specific band with an expected size of 1919 bp was found (see FIG. 2). The recovered product after double-enzyme digestion was cloned into the KpnI and XbaI restriction sites of the eukaryotic expression vector pcDNA3.1/Zeo(+), and the recombinant plasmid pcDNA3.1/Zeo(+)-B7-2-PE40 was constructed, which was subjected to plasmid extraction, electrophoresis after double-enzyme digestion (see FIG. 3) and sequencing identification (FIG. 4), so as to obtain a positive clone. The sequencing showed that the base sequence after the signal peptide had no point mutation and frame-shift mutation, which was completely consistent with the B7-2-PE40 gene sequence in the prokaryotic expression plasmid pRSETA-B7-2-PE40KDEL (see FIGS. 5A-5B), confirming that the vector was constructed successfully.

Example 3. High-Level Expression of the Constructed Therapeutic DNA Vaccine pcDNA3.1/Zeo(+)-B7-2-PE40 in Eukaryotic Cells By using liposome-mediated method, 0.5×10$^5$ to 2×10$^5$ CHO-K1-RPE.40 cells were introduced into a 24-well plate (the medium was DMEM/F12, 7.5% FBS, 1× non-essential amino acids, and was added at 0.5 ml). 0.8 µg of the plasmid and 2.0 µl of Lipofectamine™2000 were diluted with 50 µl of OPTI-MEM I medium respectively, the two were mixed and incubated for 20 min, and then slowly added to the 24-well plate. After incubation with 5% $CO_2$ at 37° C. for 6 h, the medium was replaced with complete DMEM medium. After 48 hours, the cultured cells and supernatant were collected and detected by RT-PCR and Western blotting.

RT-PCR Detection Steps:

48 h after transfection, the grown CHO-K1-RPE.40 cells were washed twice with PBS, and the total cell RNA was extracted with Trizol kit according to the instructions, then reverse transcription synthesis of cDNA was performed, PCR amplification was carried out with the above primers P1 and P2 respectively, and β-actin was used as a reference control.

The reverse transcription system was as follows:

| | |
|---|---|
| $MgCl_2$ | 2 µl |
| 10 × RNA PCR buffer | 1 µl |
| dNTP Mixture | 1 µl |
| RNase inhibitor | 0.25 µl |
| AMV | 0.5 µl |
| Oligo dT | 0.5 µl |
| RNA | 4.75 µl |
| Total volume | 10 µl |

The reaction conditions were: 42° C. for 30 min, 99° C. for 5 min, and 5° C. for 5 min.

The PCR Reaction System was as Follows:

| | |
|---|---|
| $MgCl_2$ | 3 µl |
| 10 × LA buffer | 4 µl |
| $ddH_2O$ | 31.75 µl |
| LA Taq | 0.25 µl |
| P1 | 0.5 µl |
| P2 | 0.5 µl |
| RT reactant | 10 µl |
| Total volume | 50 µl |

The reaction conditions were as follows: pre-denaturation at 96° C. for 5 min, denaturation at 96° C. for 1 min, annealing at 55° C. for 1 min, extension at 72° C. for 3 min, 30 cycles, and extension at 72° C. for 10 min. 1% agarose gel electrophoresis was used for identification.

Human β-Actin Primer Sequences were:

```
Upstream primer P5:
                          (SEQ ID NO: 4)
5' AGA AAA TCT GGC ACC ACA CC 3'

Downstream primer P6:
                          (SEQ ID NO: 5)
5' AGC ACT GTG TTG GCG TAC AG 3'
```

Western Blotting Detection Steps:
1) Protein electrophoresis: 48 h after transfection of CHO-K1-RPE.40 cells, the culture supernatant was collected and concentrated using Amicon Ultra-4. 15 µl of the sample. The culture supernatant was taken and mixed evenly with 15 µl×SDS Loading buffer, boiled for 5 minutes, and subjected to SDS-PAGE protein electrophoresis, in which 80V electrophoresis was performed until the protein was electrophoresed out of the stacking gel, and then 160V electrophoresis was performed so that it reached the bottom of the separating gel, and the power supply was disconnected.

2) Transfer membrane: Electrotransfer to PVDF membrane was performed. Immobilon-P was used as PVDF membrane, and immersed in methanol for 15 s, in water for 2 min, and in electrotransfer solution for 20 min; at the same time, filter paper and gel were immersed in electrotransfer solution for 15 min, according to +(white)/three-layer filter paper/membrane/gel/three-layer filter paper/black. The transfer membrane conditions were: 60 mA for 40 min.

3) Blocking solution was used to block at room temperature for 2 h;

4) Primary antibody diluted with blocking solution in an appropriate proportion, PEA polyclonal antibody or CD86 monoclonal antibody was added, and allowed to stand at 4° C. overnight;

5) TBST was used to wash for 3 times, 5 min each time;

6) HRP-anti-rabbit or mouse IgG secondary antibody diluted with blocking solution in appropriate proportion was added, and incubated at room temperature for 1 h;

7) TBST was used to wash for 3 times, each 10 min;

8) ECL method was used for exposure, development and fixation.

The Protein Electrophoresis Formula of the Above Step 1) was as Follows:

| | 8% separating gel (5 ml) | 5% stacking gel (2 ml) |
|---|---|---|
| $ddH_2O$ | 2.30 ml | 1.40 ml |
| 30% acrylamide | 1.30 ml | 0.33 ml |
| 1.5M Tris-HCl(PH 8.8) | 1.30 ml | — |
| 1.0M Tris-HCl(PH 6.8) | — | 0.25 ml |
| 10% SDS | 0.05 ml | 0.02 ml |
| 10% ammonium persulfate | 0.05 ml | 0.02 ml |
| TEMED | 0.003 ml | 0.002 ml |

Figure 6:
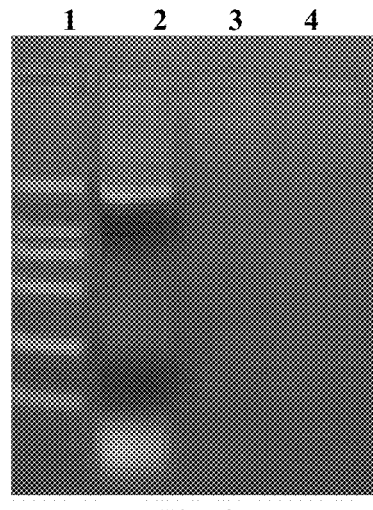
FIG. 6 shows the agarose gel electrophoresis analysis diagram of the RT-PCR product of B7-2-PE40 fusion gene after the therapeutic DNA vaccine pcDNA3.1/Zeo(+)-B7-2-PE40 eukaryotic expression vector was transfected into CHO-K1-RPE.40 cells. Among them, lane 1 is the DNA marker; lane 2 is the amplification result of B7-2-PE40 in CHO-K1-RPE.40 cells transfected with pcDNA3.1/B7-2-PE40; lanes 3 and 4 are the amplification results of CHO-K1-RPE.40 cells transfected with pcDNA3.1 empty vector.
Figure 7:
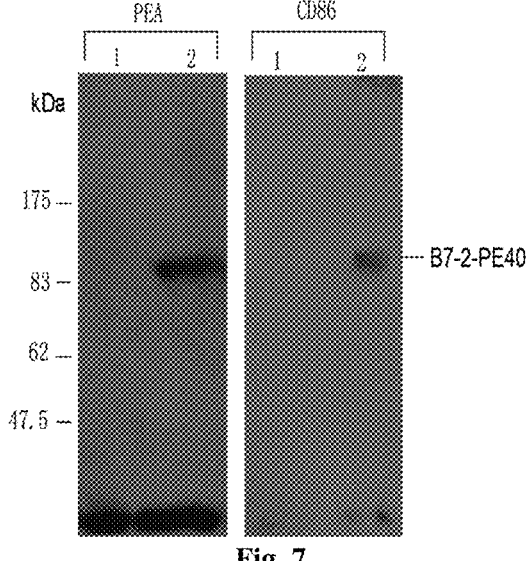
FIG. 7 shows the Western Blot detection of the target protein secreted by eukaryotic cells transfected with the therapeutic DNA vaccine pcDNA3.1/Zeo(+)-B7-2-PE40. Among them, lane 1 represents the supernatant from eukaryotic cells transfection with pcDNA3.1/Zeo(+) empty vector; lane 2 represents the supernatant from eukaryotic cells transfection with pcDNA3.1/Zeo(+)-B7-2-PE40 vector.
Figure 8:
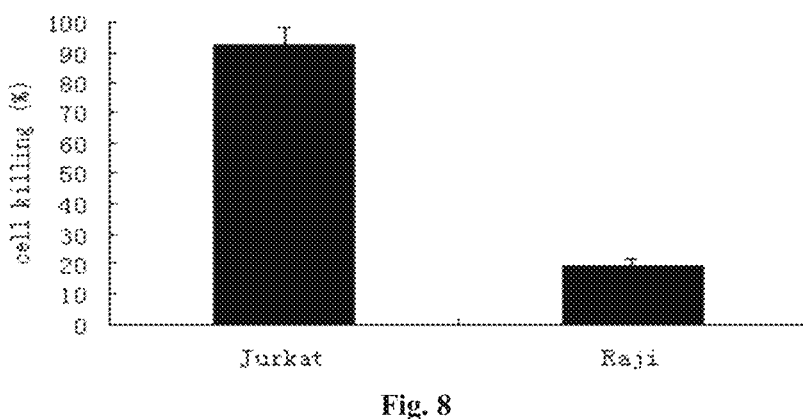
FIG. 8 shows that the expression product of eukaryotic cells stably transfected with the therapeutic DNA vaccine pcDNA3.1/Zeo(+)-B7-2-PE40 has efficient targeted killing biological activity on CD28⁺ Jurkat cells.

The pcDNA3.1/Zeo(+)-B7-2-PE40 eukaryotic expression vector correctly identified by sequencing was transiently transfected into CHO-K1-RPE.40 cells, and the expression of B7-2-PE40 fusion protein was detected by the following methods: first, RT-PCR was used to detect the synthesis of B7-2-PE40 mRNA in the transfected cells, the results were shown in FIG. 6, the CHO-K1-RPE.40 cells transfected with pcDNA3.1/Zeo(+)-B7-2-PE40 showed a specific band at 1919 bp, but the CHO-K1-RPE.40 cells transfected with the empty vector did not showed such band. The PCR amplification product of β-actin was used as an internal reference. The antigenicity and secretion expression of B7-2-PE40 fusion protein in cell culture supernatant were detected by Western blotting method. The results showed that no matter whether PEA polyclonal antibody or CD86 monoclonal antibody was used, there was a positive band at the relative molecular mass of about 90 kDa, but no band was displayed in the supernatant of cells transfected with the empty vector. The results are shown in FIG. 7. Among the screened stably transfected cells, $1\times10^6$ stably transfected cells expressed about 0.23 µg/L of B7-2-PE40 exotoxin fusion protein within 24 h (FIG. 8 and Table 1).

TABLE 1

| Detection of expression level of B7-2-PE40 exotoxin fusion protein | | |
| --- | --- | --- |
| Clone No. | $OD_{450}$ value | Protein concentration (ug/L) |
| Clone 12 | 0.624 | 0.21 |
| Clone 13 | 0.615 | 0.20 |
| Clone 14 | 0.767 | 0.27 |
| Clone 15 | 0.709 | 0.25 |

Figure 9:
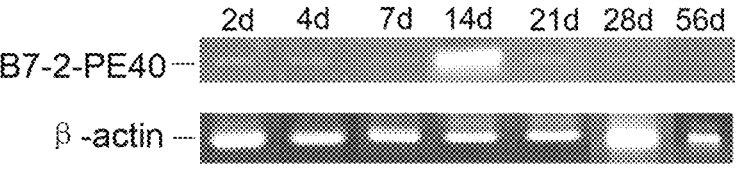
FIG. 9 shows the results of agarose electrophoresis analysis of B7-2-PE40 fusion gene after intramuscular injection of the therapeutic DNA vaccine pcDNA3.1/Zeo(+)-B7-2-PE40 plasmid in mice.
Figure 10:
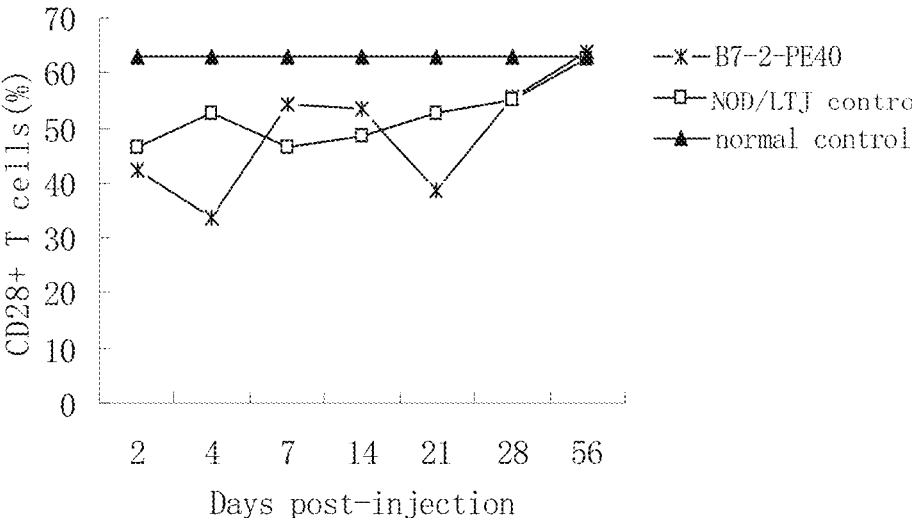
FIG. 10 shows the clearance of $CD28^+$ T cells in vivo after intramuscular injection of the therapeutic DNA vaccine pcDNA3.1/Zeo(+)-B7-2-PE40 plasmid in mice.

Example 4. Therapeutic DNA Vaccine
pcDNA3.1/Zeo(+)-B7-2-PE40 Showing Sustained
High Expression In Vivo and Highly-Efficient
Targeted Killing Biological Effect 75 to 150 μg of the purified therapeutic DNA vaccine pcDNA3.1/Zeo(+)-B7-2-PE40 plasmid was injected into the biceps femoris muscle of the right hind limb of normal Wistar rats. The mRNA of B7-2-PE40 could always be detected on day 2, 4, 7, 14, 21 and 28 after the injection, but could not be detected on day 56. The expression of B7-2-PE40 was highest on day 14 after the injection, and gradually decreased thereafter (FIG. 9). FIG. 10 showed the clearance of CD28$^+$ T cells in the peripheral blood of rats after intramuscular injection of the therapeutic DNA vaccine pcDNA3.1/Zeo(+)-B7-2-PE40 plasmid. The results showed that the T cell clearance was consistent with the expression change of B7-2-PE40 in vivo. On day 2 after the intramuscular injection, CD28$^+$ T cells were significantly killed, and the proportion thereof was lower than that of the normal and control rats. On day 4 of the treatment, CD28$^+$ T cells decreased to a minimum of 34%. There was a brief recovery after that. With the arrival of the peak expression of B7-2-PE40 on day 14, CD28$^+$ T cells decreased to the trough again on day 21. After that, the proportion of CD28$^+$ T cells gradually increased due to the decreased expression of B7-2-PE40, and returned to normal level on day 56.

Example 5. Therapeutic DNA Vaccine
pcDNA3.1/Zeo(+)-B7-2-PE40 Showing Capacity of
Effectively Reducing Blood Glucose Level in
Subject with Type 1 Diabetes Type 1 diabetes model NOD/LTJ mice were grouped for treatment and prevention (which was the same as in Example 5-8): they were divided into 4 groups in the experiment, respectively: (1) therapeutic DNA vaccine pcDNA3.1/Zeo(+)-B7-2-PE40 treatment group; (2) therapeutic DNA vaccine pcDNA3.1/Zeo(+)-B7-2-PE40 prevention group; (3) untreated control group; (4) methotrexate MTX (Jiangsu Hengrui Pharmaceutical Co., Ltd.) positive control group. Medication of the treatment group: From the eighth week when disease occurred in the type 1 diabetes model NOD/LTJ mice, the therapeutic DNA vaccine pcDNA3.1/Zeo(+)-B7-2-PE40 was intramuscularly injected once every 2 weeks for a total of three treatments. Medication of the prevention group: Form the seventh week when no disease was found in the type 1 diabetes model NOD/LTJ mice, 100 ug of the therapeutic DNA vaccine pcDNA3.1/Zeo(+)-B7-2-PE40 was intramuscularly injected once every 2 weeks for a total of four treatments. The method of intramuscular injection combined with electrical pulse stimulation (200V/cm, 20 ms, 2 Hz, 8 pulses) was adopted. For the methotrexate MTX positive control group, started within 1 week after the new disease was diagnosed, intraperitoneal injection was carried out once a week, 1.5 mg~3.0 mg/Kg for 10 consecutive weeks.

Figure 11:
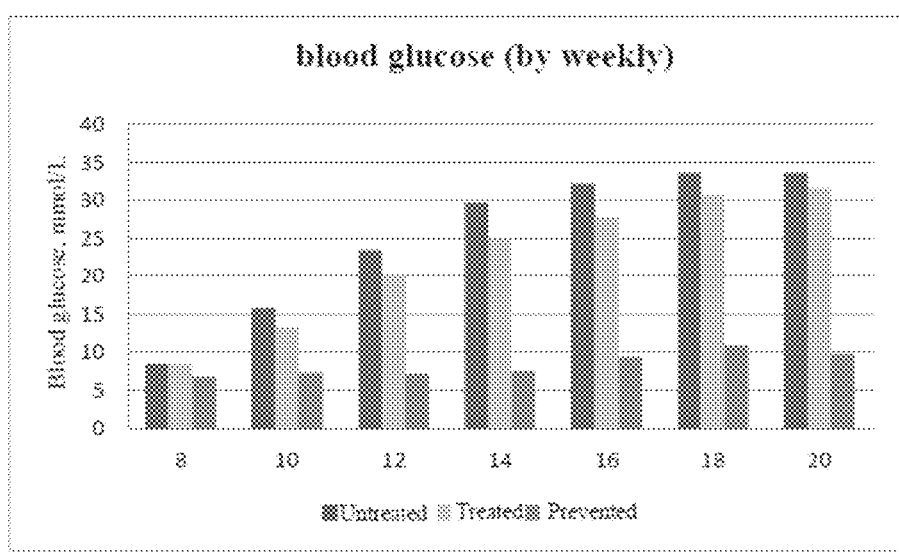
FIG. 11 shows the change of blood glucose in NOD/LTJ mice with type 1 diabetes treated and prevented by the therapeutic DNA vaccine pcDNA3.1/Zeo(+)-B7-2-PE40.

Treatment group: From the eighth week when disease was occurred in the type 1 diabetes model NOD/LTJ mice, 150 ug of the therapeutic DNA vaccine pcDNA3.1/Zeo(+)-B7-2-PE40 plasmid was intramuscularly injected once every 2 weeks for a total of three treatments. The results showed that the therapeutic DNA vaccine pcDNA3.1/Zeo(+)-B7-2-PE40 could not only effectively treat type 1 diabetes model NOD/LTJ mice, but also reduce blood glucose, and its effect was significantly better than that of methotrexate MTX positive control. Especially in the prevention group, from the seventh week when no disease was found in the type 1 diabetes model NOD/LTJ mice, 100 ug of the therapeutic DNA vaccine pcDNA3.1/Zeo(+)-B7-2-PE40 was intramuscularly injected once every 2 weeks for a total of four preventive medications. The therapeutic DNA vaccine pcDNA3.1/Zeo(+)-B7-2-PE40 could very significantly prevent the occurrence and development of disease in the type 1 diabetes model NOD/LTJ mice, and maintain the blood glucose content at normal levels in the type 1 diabetes model NOD/LTJ mice (FIG. 11).

Blood glucose monitoring step: Using an integrated micro whole blood glucose meter (purchased from Roche), weekly micro whole blood glucose measurement was performed on the above-mentioned type 1 diabetes model NOD/LTJ mice and balb/c normal mice. Diabetes was diagnosed when blood glucose was measured as >11.3-13.9 mmol/L for successive two times. The micro whole blood glucose measurement was performed weekly from week 8. Special attention was paid to the changes of blood glucose in the type 1 diabetes model NOD/LTJ mice after the treatment with the therapeutic DNA vaccine pcDNA3.1/Zeo(+)-B7-2-PE40, in order to evaluate the therapeutic effect of the therapeutic DNA vaccine in the type 1 diabetes model NOD/LTJ mice.

The specific method of taking blood from tip of tail was as follows: this method of taking blood by cutting tail was adopted when the required blood volume was very small, in which the animal was fixed to expose rat tail, the tail was shaved to remove hair and then sterilized, and then immersed in warm water at about 45° C. for several minutes to fill the tail vessels; then the tail was wipe dried, and a sharp tool (knife or scissors) was used to cut off the tip of the tail, 0.3-0.5 cm, the integrated blood glucose meter was opened and a test strip was used to take blood spot, when the blood glucose meter emitted a signal sound, reading was carried out, the blood collection was over, and the wound was disinfected and pressed to stop bleeding.

Example 6. Therapeutic DNA Vaccine
pcDNA3.1/Zeo(+)-B7-2-PE40 Showing Capacity of
Effectively Increasing Blood Insulin Level in
Subject with Type 1 Diabetes The serum insulin levels of the experimental group and the control group were detected by Elisa kit, and the detection was performed at different time periods, such as the $10^{th}$ week in the early stage of the experiment, the $12^{th}$ week in the early stage of the experiment, the $14^{th}$ week in the middle stage of the experiment, and the $16^{th}$ week in the late stage of the experiment. Special attention was paid to the changes of insulin level in the type 1 diabetes model NOD/LTJ mice after treatment with the therapeutic DNA vaccine pcDNA3.1/Zeo(+)-B7-2-PE40, so as to evaluate the therapeutic effect of the therapeutic DNA vaccine in the type 1 diabetes model NOD/LTJ mice.

15                                                                                          16

The method of taking blood from orbital venous plexus was as follows: after obtaining fresh blood, it was placed in an EDTA anticoagulant tube selected according to the requirements of the specimen, mixed for 10-20 minutes, and centrifuged for about 20 minutes (2000-3000 rpm). The supernatant was collected carefully, and it should be centrifuged again if a precipitate formed during storage. The ELISA kit contained a 96-well plate that had been coated with antibodies, and the reaction results were determined by an enzyme-linked reaction apparatus. The concentrations of the standard substance were used as the abscissa and the OD values were used as the ordinate, thus the standard curve was drawn on graph paper, and the corresponding concentration was found out from the standard curve according to the OD value of the sample; it was then multiplied by its dilution factor; alternatively, the concentrations and OD values of the standard substance were used to calculate the linear regression equation of the standard curve, then the OD value of the sample was substituted into the equation to calculate the concentration of the sample, which was multiplied by its dilution factor to obtain the actual concentration of the sample.

Figure 12:
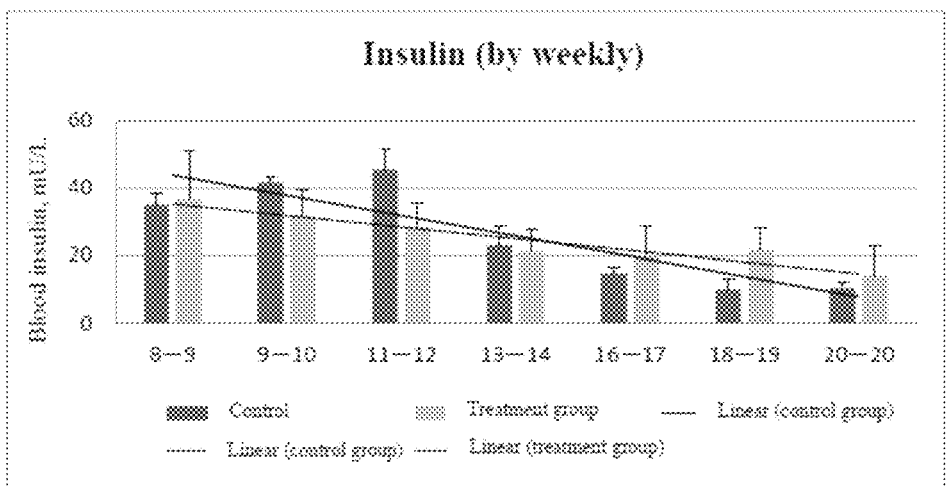
FIG. 12 shows the change of blood insulin content in NOD/LTJ mice with type 1 diabetes treated with the therapeutic DNA vaccine pcDNA3.1/Zeo(+)-B7-2-PE40.
Figure 13:
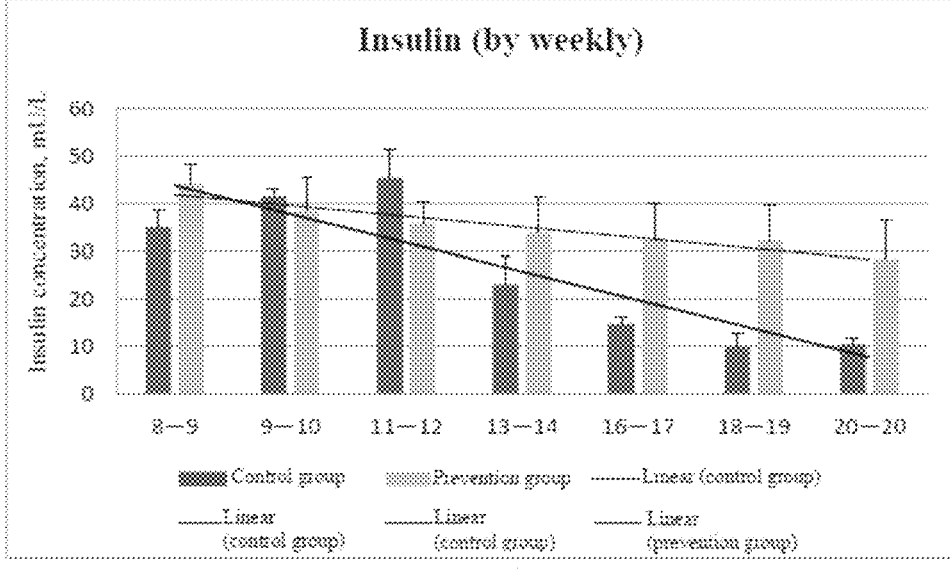
FIG. 13 shows the change of blood insulin content in NOD/LTJ mice with type 1 diabetes prevented by the therapeutic DNA vaccine pcDNA3.1/Zeo(+)-B7-2-PE40.

Treatment group: From the eighth week when disease occurred in the type 1 diabetes model NOD/LTJ mice, 150 ug of the therapeutic DNA vaccine pcDNA3.1/Zeo(+)-B7-2-PE40 plasmid was intramuscularly injected once every 2 weeks for a total of three treatments. The results showed that the therapeutic DNA vaccine pcDNA3.1/Zeo(+)-B7-2-PE40 could effectively treat the NOD/LTJ mice, significantly increase the blood insulin content, and its effect was significantly better than that in the methotrexate MTX positive control (FIG. 12). Especially in the prevention group, from the seventh week when no disease was not found in the type 1 diabetes model NOD/LTJ mice, 100 ug of the therapeutic DNA vaccine pcDNA3.1/Zeo(+)-B7-2-PE40 was intramuscularly injected once every 2 weeks for a total of four preventive medications. The therapeutic DNA vaccine could more significantly increase the blood insulin level (FIG. 13).

Figure 14:
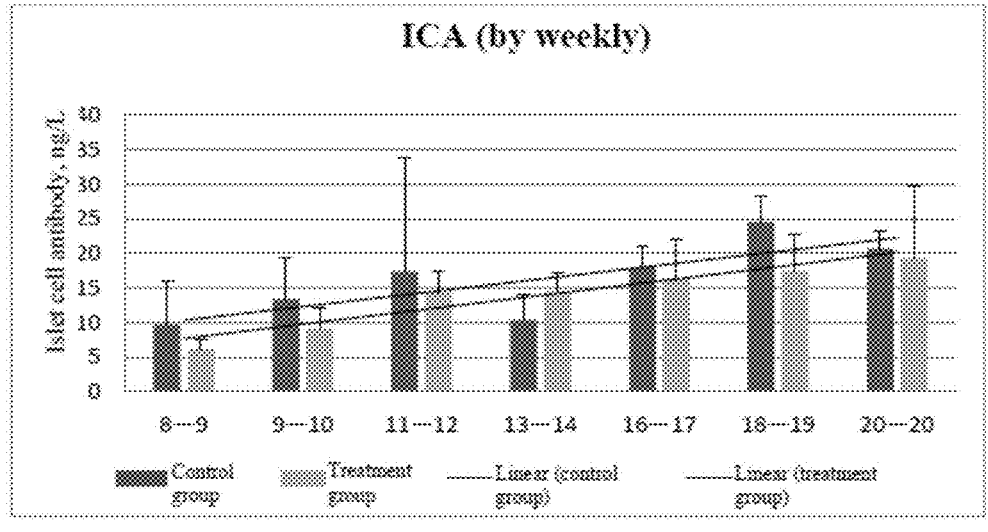
FIG. 14 shows the change of blood ICA autoantibody in NOD/LTJ mice with type 1 diabetes treated with the therapeutic DNA vaccine pcDNA3.1/Zeo(+)-B7-2-PE40.
Figure 15:
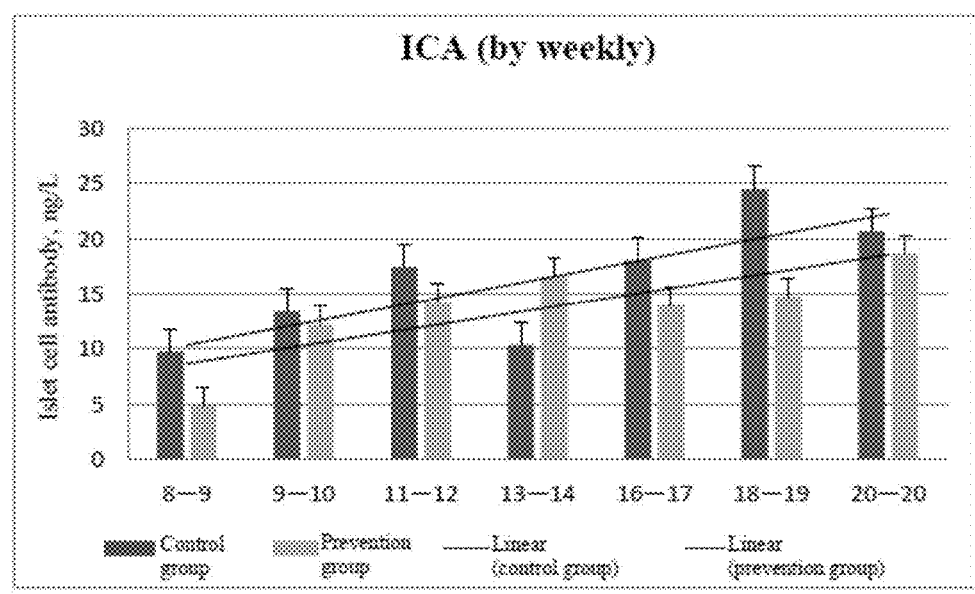
FIG. 15 shows the change of blood ICA autoantibody in NOD/LTJ mice with type 1 diabetes prevented by the therapeutic DNA vaccine pcDNA3.1/Zeo(+)-B7-2-PE40.

Example 7. Therapeutic DNA Vaccine pcDNA3.1/Zeo(+)-B7-2-PE40 Showing Capability of Effectively Reducing Concentration of Autoantibody ICA in Subject with Type 1 Diabetes Treatment group: From the eighth week when disease occurred in the type 1 diabetes model NOD/LTJ mice, 150 ug of the therapeutic DNA vaccine pcDNA3.1/Zeo(+)-B7-2-PE40 plasmid was intramuscularly injected once every 2 weeks for a total of three treatments. Prevention group:

From the seventh week when no disease was found in the type 1 diabetes model NOD/LTJ mice, 100 ug of the therapeutic DNA vaccine pcDNA3.1/Zeo(+)-B7-2-PE40 was intramuscularly injected once every 2 weeks for a total of four preventive medications. The change of serum ICA level in the type 1 diabetes model NOD/LTJ mice was detected by Elisa method. The results showed that the therapeutic DNA vaccine pcDNA3.1/Zeo(+)-B7-2-PE40 could not only effectively treat the occurrence and development of disease in the type 1 diabetes model NOD/LTJ mice, but also effectively reduce the blood concentration of ICA autoantibody in the type 1 diabetes model NOD/LTJ mice; both the treatment group and the prevention group showed the same effects, which were significantly better than that of the methotrexate MTX positive control (FIG. 14 and FIG. 15).

Figure 16:
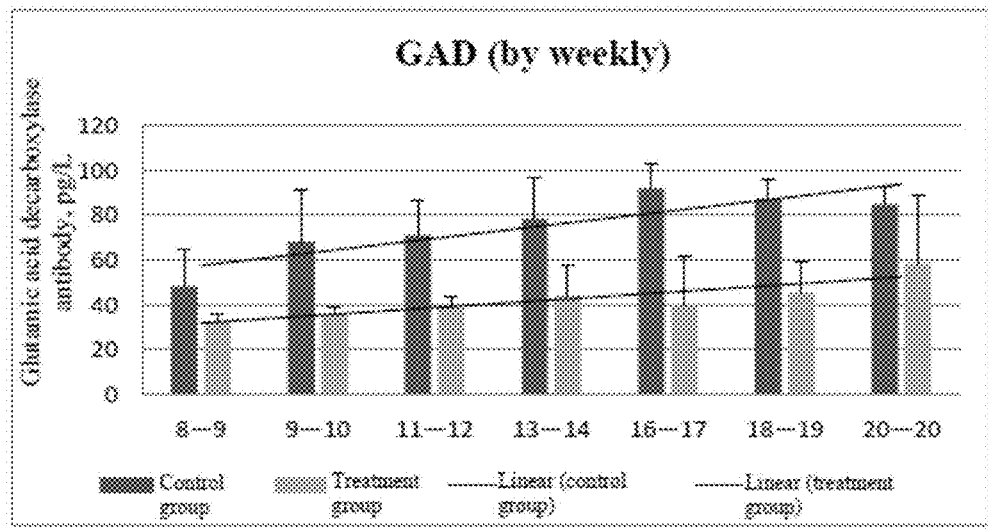
FIG. 16 shows the change of blood GAD autoantibody in NOD/LTJ mice with type 1 diabetes treated with the therapeutic DNA vaccine pcDNA3.1/Zeo(+)-B7-2-PE40.
Figure 17:
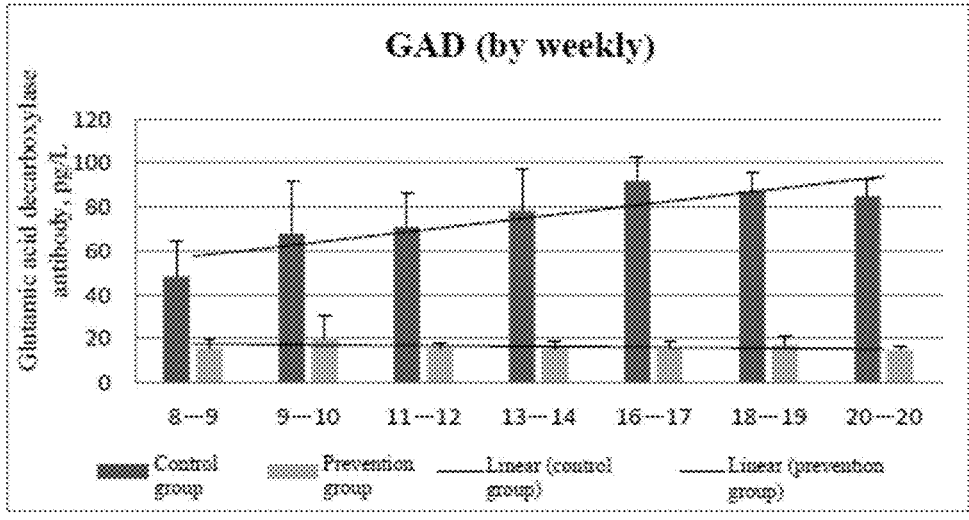
FIG. 17 shows the change of blood GAD autoantibody in NOD/LTJ mice with type 1 diabetes prevented by the therapeutic DNA vaccine pcDNA3.1/Zeo(+)-B7-2-PE40.

Example 8. Therapeutic DNA Vaccine pcDNA3.1/Zeo(+)-B7-2-PE40 Showing Capacity of Effectively Reducing Concentration of Autoantibody GAD in Subject with Type 1 Diabetes Treatment group: From the eighth week when disease occurred in the type 1 diabetes model NOD/LTJ mice, 150 ug of the therapeutic DNA vaccine pcDNA3.1/Zeo(+)-B7-2-PE40 plasmid was intramuscularly injected once every 2 weeks for a total of three treatments. Prevention group: From the seventh week when no disease was found in the type 1 diabetes model NOD/LTJ mice, 100 ug of the therapeutic DNA vaccine pcDNA3.1/Zeo(+)-B7-2-PE40 was intramuscularly injected once every 2 weeks for a total of four preventive medications. The change of blood GAD level in the type 1 diabetes model NOD/LTJ mice was detected by Elisa method. The results showed that the therapeutic DNA vaccine pcDNA3.1/Zeo(+)-B7-2-PE40 could not only effectively treat the occurrence and development of disease in the type 1 diabetes model NOD/LTJ mice, but also significantly reduce the blood concentration of GAD autoantibody in the type 1 diabetes model NOD/LTJ mice, which were significantly better than that of the methotrexate MTX positive control, and especially remarkable for the prevention group (FIG. 16 and FIG. 17).

The present invention has been described in detail above, and its purpose is to enable those skilled in the art to understand the content of the present invention and implement it, and not to limit the scope of protection of the present invention, all equivalent variations or modifications made according to the spirit of the present invention are intended to be included within the scope of the present invention.

What is claimed is:

1. A method for treating type 1 diabetes in a subject, the method comprising administering to the subject suffering the type 1 diabetes an effective amount of (a) a recombinant nucleic acid construct comprising a B7-2-PE40 (*Pseudomonas* exotoxin A 40 kD) exotoxin fusion gene, wherein the B7-2-PE40 exotoxin fusion gene has the sequence as shown in SEQ ID NO:1; or (b) therapeutic DNA vaccine or a pharmaceutical composition comprising said recombinant nucleic acid construct.

2. The method according to claim 1, wherein the B7-2-PE40 exotoxin fusion gene is operably ligated to a recombinant expression vector, and the recombinant expression vector is selected from the group consisting of pcDNA3.1/Zeo(+), pVAX1, pWLNEO, pSV2CAT, pOG44, pXT1, pSG, pSVK3, pBPV, pMSG, pSVL and adenovirus vector.

3. The method according to claim 2, the recombinant expression vector is pcDNA3.1/Zeo(+).

4. The method according to claim 1, wherein the therapeutic DNA vaccine further comprises a pharmaceutically acceptable immune adjuvant.

5. The method according to claim 1, wherein the subject is immunized with the recombinant nucleic acid construct or the therapeutic DNA vaccine by injection, mucosa, or gene gun introduction.

6. The method according to claim 1, wherein the subject is immunized with the recombinant nucleic acid construct or the therapeutic DNA vaccine by a manner selected from the group consisting of intravenous injection, intra-arterial injection, intramuscular injection, subcutaneous injection, organ injection, intrathoracic injection and intraperitoneal injection.

7. The method according to claim 1, wherein the therapeutic DNA vaccine is an aqueous solution or a lyophilized powder for reconstitution for injection or mucosal administration.

8. The method of claim 1, wherein the pharmaceutical composition further comprises a pharmaceutically acceptable carrier.

9. The method of claim 1, wherein the subject is a mammal.

10. The method of claim 1, wherein the subject is a human.

*   *   *   *   *